(12) United States Patent
Jordan Navas et al.

(10) Patent No.: US 11,648,565 B2
(45) Date of Patent: May 16, 2023

(54) EQUIPMENT AND METHOD FOR THE AUTOMATED MANAGEMENT OF BIOLOGICAL SAMPLE JARS

(71) Applicant: DREAMPATH DIAGNOSTICS, Strasbourg (FR)

(72) Inventors: Pablo Jordan Navas, Madrid (ES); Valerie Wilhelm, Eschau (FR)

(73) Assignee: DREAMPATH DIAGNOSTICS, Strasbourg (FR)

( * ) Notice: Subject to any disclaimer, the term of this patent is extended or adjusted under 35 U.S.C. 154(b) by 185 days.

(21) Appl. No.: 16/990,175

(22) Filed: Aug. 11, 2020

(65) Prior Publication Data
US 2021/0060563 A1 Mar. 4, 2021

(30) Foreign Application Priority Data
Aug. 30, 2019 (FR) ..................................... 19 09562

(51) Int. Cl.
*B01L 3/00* (2006.01)
*G16H 10/40* (2018.01)

(52) U.S. Cl.
CPC ........... *B01L 3/545* (2013.01); *B01L 3/50853* (2013.01); *G16H 10/40* (2018.01); *B01L 2300/022* (2013.01)

(58) Field of Classification Search
CPC ...... B01L 3/54; B01L 3/545; B01L 2300/021; B01L 2300/022; B01L 2300/023; B01L 2300/024; G01N 35/00613; G01N 35/00722; G01N 35/0099; G01N 35/025; G01N 2035/00643; G01N 2035/00801; G01N 2035/00821; G01N 2035/00831; G01N 2035/00841
See application file for complete search history.

(56) References Cited

U.S. PATENT DOCUMENTS

| | | | |
|---|---|---|---|
| 2014/0273242 A1* | 9/2014 | Ochranek | ............ G01N 35/025 422/65 |
| 2017/0177913 A1* | 6/2017 | Benedetti | ............... G16H 10/40 |
| 2018/0364270 A1* | 12/2018 | Chiu | ................ G01N 35/00069 |

FOREIGN PATENT DOCUMENTS

| | | |
|---|---|---|
| EP | 3 182 310 A1 | 6/2017 |
| WO | 2015 040320 A1 | 3/2015 |

* cited by examiner

*Primary Examiner* — Jill A Warden
*Assistant Examiner* — Dwayne K Handy
(74) *Attorney, Agent, or Firm* — Craft Chu PLLC; Andrew W. Chu

(57) ABSTRACT

The equipment item for automatically managing a plurality of biological samples placed in a respective sample jar includes a storage container for sample jars having a plurality of housings, an apparatus with a reader of encoded identification data affixed on the sample jars placed in the container, a device for determining data representative of the position of each sample jar within the container, and a device for rotating the container, and a computer processor connected to the apparatus. The container includes, in the immediate vicinity of each housing, a shape appearing recessed or raised, while the device for determining data representative of the position of each sample jar is defined by a detector for the shape.

12 Claims, 1 Drawing Sheet

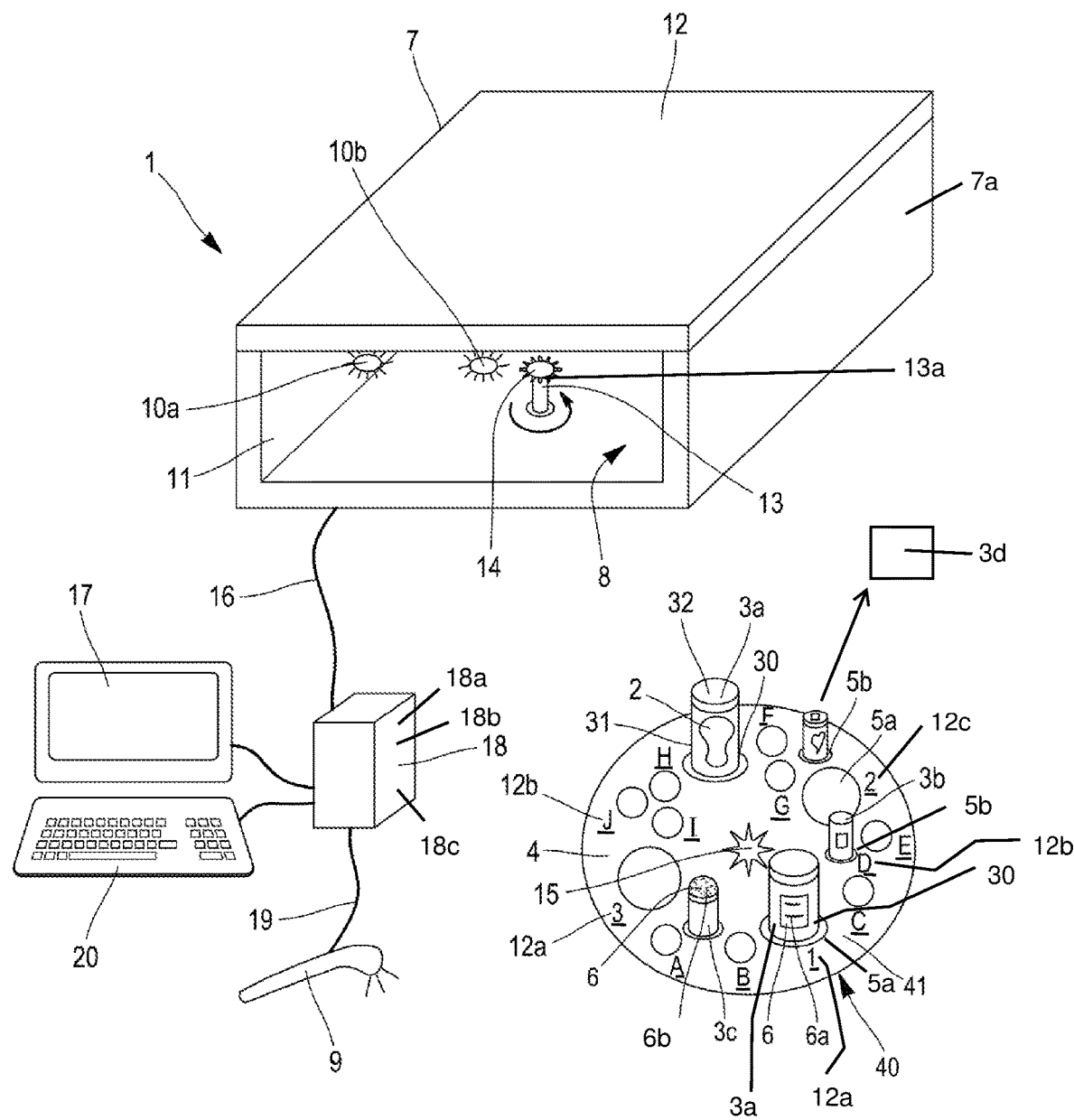

EQUIPMENT AND METHOD FOR THE AUTOMATED MANAGEMENT OF BIOLOGICAL SAMPLE JARS

CROSS-REFERENCE TO RELATED APPLICATIONS

See Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The present invention relates to equipment and a method for the automated management of a plurality of biological samples each placed in a sample jar for analyses intended to make a diagnosis.

2. Description of Related Art Including Information Disclosed Under 37 CFR 1.97 and 37 CFR 1.98

Conventionally, pathology laboratories receive freshly collected biological samples each day, which are placed in jars of formalin of different sizes, which they record in their computer system before subjecting them to different analysis methods. The latter are selected on a case-by-case basis and commonly involve a veritable journey by these biological samples through the laboratories, through which they are handled by different specialists or technicians and are therefore moved several times.

In practice, in the best case scenario, analyses done in a single step from all of the material taken from a same patient, and therefore all of the material contained in a same jar, can lead to the establishment of a reliable diagnosis.

However, one or several steps consisting of studying the material, fraction after fraction, using different methods, are often necessary to obtain a diagnosis that is considered to be satisfactory.

Typically, large surgical specimens, only some parts of which seem a priori to be relevant to establish a diagnosis, can be affected by such treatment. In fact, additional analyses, conducted from new fractions, regularly prove necessary, and therefore presume finding the initial jar in which the remaining part is kept to continue the investigations.

Whatever the case may be, the regulations in force require the pathology laboratories to keep any fraction initially discarded from the analysis process, in the original sample jar, until the final diagnosis is made, so as to be able to use it a second time, and to perform any additional analyses.

Furthermore, in some cases, secondary cytological examinations prove necessary in order to confirm or reject the results of primary tests, and also presume storage of the biological sample in question, until the final result, in its original formalin jar.

Biological samples of the biopsy type are generally extracted as is in their entirety from the formalin jar in order to be integrated into a block of paraffin, next making it possible to produce slides for microscopic observation. However, it should be noted that some jars may contain several biopsies taken from a same patient, which may lead to several paraffin blocks produced spread out over time. Such biopsies must also remain kept in the formalin of the initial sample jar until the set of blocks is produced.

It emerges from the preceding that pathology laboratories are faced with a first organizational constraint, assuming the possibility of quickly and reliably locating a biological sample, and therefore the sample jar in which it is kept, in order to make or finalize diagnoses and propose suitable treatments, while sparing patients from new, untimely samples caused by a potential loss of material, and which may generate significant stress.

Furthermore, in all cases, after a mandatory retention period, which conventionally ends two to four weeks after publication of the diagnosis report, the sample jars and any residues of biological material that they still contain can be destroyed, which in particular makes it possible to free up space to accommodate new jars and to work in an environment with the best possible organization.

Being able to identify and locate the sample jars to be destroyed quickly and reliably represents a second challenge for pathology laboratories, which currently have no streamlined solution or any equipment specifically designed to achieve this aim. Indeed, conventionally, the jars present within laboratories are simply stored in a jumble in baskets, allowing them to be transported together, and remain there throughout the process. At the end of the process, manual sorting, done by a list generated via the laboratories' computer system, is generally required, making it possible to remove the sample jars authorized for destruction from these baskets. Clearly, such an approach is tedious and in no way eliminates the risk of error.

In short, at this time, pathology laboratories are losing considerable time and efficiency, since they have no streamlined solution for managing the biological sample jars for which they are responsible. This situation may be further aggravated by the fact that the number of jars to be processed is constantly increasing, due inter alia to the aging of the population and the increased incidence of certain diseases, such as cancer in particular.

BRIEF SUMMARY OF THE INVENTION

The aim of the present invention is to propose equipment and a method specifically designed to allow streamlined management of biological samples and the jars containing them by pathology laboratories or by any equivalent department responsible for performing analyses and preparing diagnoses. More specifically, one aim of the invention is to propose equipment and a method making it possible to guarantee the traceability of biological samples contained in sample jars, throughout their entire storage duration in such jars, and to quickly and automatically extract them from their storage location, then destroy them at the appropriate moment with no risk of error and losses of samples that may prove detrimental for patients.

To that end, the present invention relates to an equipment item for automatically managing a plurality of biological samples each placed in a sample jar including a bottom topped by a peripheral wall and closed by a lid, said equipment item including:
  at least one storage container for sample jars having a plurality of housings with a shape complementary to a bottom of a sample jar,
  at least one apparatus assuming the form of a case delimiting a cavity configured to accommodate at least one container, and equipped with means for reading encoded identification data affixed on the peripheral wall and/or the lid of the sample jars placed in said container, means for determining data representative of the position of each sample jar within said container, as well as means for rotating the container,
  computer processing means connected to said apparatus by wired or wireless data transmission means and incorporating a software application run in order to record in memory means, for each jar, in an associated manner, the identification data that it includes, the data representative of its position within the container and data relative to a history of the biological sample that it contains,
  detect the occurrence of a given event in the history of each jar and generate, via a user interface, a list indicating the identification data of the jars for which the event is detected and their position within the container, characterized in that the container includes, in the immediate vicinity of each housing, a shape appearing recessed or raised, while the means for determining data representative of the position of each sample jar within said container are defined by means for detecting any said shape.

According to a first feature of the invention, the means for rotating the container are defined by a shaft mounted rotating in the cavity of said apparatus, while the container consists of a plate having a lower face and an upper face including said housings, said shaft and said plate having means for temporary assembly of the plate to the shaft, which are designed able to block the rotation of the plate relative to said shaft.

According to one conceivable variant embodiment, the assembly means include an end piece of polygonal section extending one free end of the shaft and an orifice having a shape complementary to the section of the endpiece extending from the lower face of the plate through at least part of the thickness of the latter.

Furthermore, in order to have a container for universal use, it has been conceived to equip the latter with housings having variable shapes and dimensions relative to one another, and therefore simultaneously able to accommodate jars with different shapes and sizes.

Advantageously, said housings and/or said sample jars can further include mistake-proofing means making it possible to ensure suitable positioning of a jar in a housing. Such a feature makes it possible to limit any reading problems or defects of the encoded data by the reading means with which the apparatus is equipped, owing to an adequate orientation of the jars toward said reading means.

The equipment item according to the invention is further characterized in that it includes an additional encoded data reader connected to said computer processing means. In the case at hand, it has been conceived to complete the equipment item with an additional encoded data reader, in particular of the barcode scanner type, allowing a rapid verification of the content of a sample jar stored in a given storage means. Such a barcode scanner can further have a display screen allowing an operator to view the results of his verifications directly thereon.

Additionally, according to the invention, the equipment item can further include at least one furniture component designed to be able to house a plurality of containers.

Furthermore, it has also been considered for the container with which the equipment item according to the invention is provided to include means for indicating the position of jars for which a given event is detected, said indicating means being connected to the computer processing means.

One additional feature of the equipment item according to the invention is defined by the fact that it may include means for automatically extracting jars from said container for which a given event is detected, said automatic extraction means being connected to the computer processing means.

The invention also relates to a method for automatically managing a plurality of biological samples each placed in a sample jar including a bottom topped by a peripheral wall and closed by a lid using the equipment item according to any one of the preceding claims, characterized in that the following steps are carried out:
  A plurality of sample jars bearing identification data affixed on their peripheral wall and/or their lid are placed in the housings of at least one container,
  For each jar placed in said container, its identification data, the data representative of its position within the container and data relative to a history of the biological sample that it contains are read and recorded using said apparatus and said computer processing means, in an associated manner,
  The software application of the computer processing means is configured such that it detects the occurrence of a given event in the data relative to the history of the biological sample contained in each jar,
  A list is displayed on the user interface indicating the identification data of the jars for which said given event is detected and their position within the container,
  The jars for which the given event is detected are removed from said container, and they are destroyed, characterized in that in order to read the data representative of the position of each sample jar within said container, detection means of any form are used, appearing in recessed or raised, in the immediate vicinity of each housing.

The method according to the invention is also characterized in that during the detection of said given event, indicating means are automatically triggered for the position of the jars to be extracted included by said container.

Furthermore, one additional feature consists in that during the detection of said given event, means are triggered for automatic extraction of the jars from the container of the equipment item.

BRIEF DESCRIPTION OF THE SEVERAL VIEWS OF THE DRAWINGS

The present invention will be described in more detail in the following disclosure, done in reference to the appended FIGURE, provided as a non-limiting example, and illustrating a simplified view of a variant embodiment of the equipment item according to the invention.

The FIGURE shows a schematic view of the equipment and method of the present invention.

DETAILED DESCRIPTION OF THE INVENTION

As indicated above, the present invention relates to an equipment item 1 for automatically managing a plurality of biological samples 2 each placed in a sample jar 3a, 3b, 3c, etc., generally of tubular shape, including a bottom 30 topped by a peripheral wall 31 and closed by a lid 32.

As illustrated in the FIGURE, the equipment item or system 1 includes at least one storage container 4 for sample jars 3a, 3b, 3c, etc., (sample jar 3a, another sample jar 3b) defined here by a plate 40a having a lower face 40, and an upper face 41 in which a plurality of housings 5a, 5b, 5c (first housing 5a, second housing 5b) in the form of recesses, with a shape complementary to a bottom 30 of a sample jar 3a, 3b, 3c, etc., have been arranged. Conventionally, after inserting a biological sample 2 into a jar 3a, 3b, 3c, etc., encoded identification data, for example in the form of a barcode or matrix code 6a or RFID chip 6b, are affixed directly on the peripheral wall 31 or the lid 32 of each jar, or using an adhesive sticker 6 adhered on one and/or the other of these same locations. It should be noted that in the illustrated variant embodiment, the housings 5a, 5b, 5c, etc. have variable shapes and sizes relative to one another, which makes it possible to store sample jars 3a, 3b, 3c, etc. with variable shapes and sizes in a same container 4.

The equipment item 1 further includes at least one apparatus, assuming the form of a case 7, delimiting a cavity 8, molded to accommodate at least one container 4. The cavity 8 is equipped with reading means 10a, 10b for encoded identification data affixed on the peripheral wall 31 and/or the lid 32 of the sample jars 3a, 3b, 3c, etc., placed in the container 4. These reading means can for example be defined by one or several light scanners 10a, 10b for encoded data, in particular of the barcode or matrix code type 6a, or RFID reader(s), mounted appropriately in the cavity 8, for example on the peripheral wall 11 or the lid 12 of the case delimiting the cavity 8.

Additionally, the apparatus 7 also includes means 10a, 10b for reading position markings or means for determining data representative of the position of each sample jar 3a, 3b, 3c, etc., within the container 4, for example means for detecting numbers 12a or letters 12b, or any other type of shape as position markings 12a, 12b (first position marking 12a, second position marking 12b), appearing raised or recessed in the immediate vicinity of each housing 5a, 5b, 5c, etc. These means for determining data representative of the position of each sample jar 3a, 3b, 3c, etc. can be independent of the reading means 10a, 10b for reading encoded data. However, in addition to the function of reading encoded data, the latter can be designed such that they can also perform the function of detecting and reading shapes appearing raised or recessed near said housings 5a, 5b, 5c, etc.

It should further be noted that means for rotating the container 4, defined by a shaft 13 mounted rotating in the cavity 8 of the apparatus 7, make it possible, when a container 4 provided with jars 3a, 3b, 3c, etc. is inserted into the apparatus 7, to orient each jar successively across from reading means 10a, 10b so that the latter read encoded data affixed on the lid 32 or the peripheral wall 31 thereof, and optionally the data 12a, 12b, representative of the position of each sample jar 3a, 3b, 3c, etc., on the container 4, or otherwise also opposite means for determining data representative of the position of each sample jar when they are independent of the reading means 10a, 10b.

In this respect, it can advantageously be provided that the housings 5a, 5b, 5c, etc. and/or the sample jars 3a, 3b, 3c, etc. include mistake-proofing means making it possible to ensure suitable positioning of the jars 3a, 3b, 3c, etc., in the housings 5a, 5b, 5c, etc., in terms of orientation of the encoded data toward the reading means 10a, 10b for reading the encoded data. In short, such mistake-proofing means allow an operator responsible for positioning the jars 3a, 3b, 3c, etc., in the plate 4, to arrange the latter spontaneously and without trial and error such that the sticker 6 that they include is systematically oriented toward the reading means 10a, 10b when each jar arrives opposite the latter.

Another feature of the invention is defined by the fact that the shaft 13 and the container 4 have temporary assembly means including, in the illustrated example, an end piece 14 of polygonal section extending a free end 13a of the shaft 13 and an orifice 15 having a shape complementary to the section of the end piece 14 extending from the lower face 40 toward the upper face 41 of the plate 4. Thus, the container 4 is stationary relative to the shaft 13 and inevitably follows the rotational movement of the latter during the operation of the apparatus 7.

Furthermore, the equipment item 1 is completed by computer processing means, of the computer 18 type, connected to the apparatus 7 by wired or wireless data transmission means 16 and incorporating a software application 18b, a processor 18a, and a memory 18c in order to
- record in memory means, for each jar 3a, 3b, 3c, etc., in an associated manner, the identification data that it includes, the data 12a, 12b representative of its position within the container 4 and data relative to a history of the biological sample that it contains,
- detect the occurrence of a given event in the history of each jar 3a, 3b, 3c, etc., and
- generate, via a user interface, such as a screen 17, a list indicating the identification data of the jars 3a, 3b, 3c, etc. for which the event is detected as well as their position 12a, 12b within the plate 4.

An additional encoded data reader 9, in particular of the manual barcode reader type, connected to said computer processing means by a wired or wireless connection 19, is also provided in the illustrated variant embodiment of the equipment item according to the invention. As previously indicated, such a barcode reader can advantageously incorporate a screen allowing immediate reading of the read data.

Furthermore, the plate 4 can also include means for indicating the position of the jars 3a, 3b, 3c for which a given event is detected, in particular such as lighted indicators and/or means for emitting sound signals implanted on the plate 4 near each housing 5a, 5b, 5c. The activation by the computer processing means of one or several of these indicating means allows an operator to immediately detect the jar(s) 3a, 3b, 3c to be extracted, without having to consult the list displayed on the screen 17 of the computer 18.

Additionally, means for automatically extracting jars 3a, 3b, 3c from said plate 4 for which a given event has been detected can further advantageously complete the equipment item 1.

Advantageously, the equipment item according to the invention can further include at least one furniture component, for example a box or cabinet, provided with drawers or rails, designed to house a plurality of plates 4, for example superimposed in drawers or secured to rails and then extending in one or several columns. In this respect, a variant embodiment can be provided in which the equipment item includes a gripping arm, controlled by the computer processing means, and designed to be capable of extracting jars 3a, 3b, 3c from plates 4, which in turn are stored in such a furniture component.

In practice, the equipment item 1 according to the invention allows a streamlined and automated management of sample jars 3a, 3b, 3c, etc., by the competent pathology or medical analysis departments, through the implementation of simple, effective and reliable steps consisting of:

Placing, when they arrive within a laboratory, a plurality of sample jars 3a, 3b, 3c, etc. bearing identification data 6a affixed on their peripheral wall 31 and/or their lid 32 are placed in the housings 5a, 5b, 5c corresponding to the shape of the jars in question, of at least one plate 4, For each jar 3a, 3b, 3c, etc. placed in the plate 4, reading and recording, using the apparatus 7 and computer processing means 18, in an associated manner, its identification data 6a, the data 12a, 12b representative of its position within the container 4 and the data representative of the history of the biological sample that it contains. More specifically, the latter can be introduced manually into the computer processing means 18 for example using a keyboard 20, and correspond to all of the events related to the biological samples placed in the jars (sample date, analysis date (s), issue date of the diagnosis report, etc.), Configuring the software application of the computer processing means 18 such that it detects the occurrence of a given event in the data relative to the history of the biological sample contained in each jar, this given event for example being defined by a date t corresponding to the date t0 on which a diagnosis report relative to a biological sample was issued plus a period t1, for example at least equal to two weeks.

Recovering on the screen 17, or if applicable that of the barcode reader 9, a list indicating the identification data of the jars for which the given event is detected and their position within the container 4, or identifying said jars on the latter through visual and/or sound indicating means that it includes, And lastly extracting from the plate 4, if applicable by implementing an automatic extraction means, the jars 3a, 3b, 3c, etc., for which the given event is detected, in order to destroy them.

In other words, the equipment item 1 according to the invention makes it possible to have information at all times regarding the location of a given biological sample owing to streamlined storage of the sample jars in containers and, if applicable, in dedicated furniture components, and the storage, in the computer system, of the position of each jar, associated with identification data that it includes through the apparatus 7. Thus, it is possible to find a given sample quickly, easily by querying the computer system and locating the cabinet if applicable, the plate 4 then the corresponding location on the latter. At this stage, a verification, through a scan done manually with the barcode scanner 9 can be done by an operator in order to guarantee that the located jar indeed contains the desired biological sample.

Furthermore, the equipment item according to the invention also makes it possible to facilitate the sorting of the jars and to quickly separate the jars to be destroyed from those that are to be kept, the latter no longer being stored in a jumble in baskets, but carefully stored on plates 4 or in containers including housings that are easily identifiable and associated with said jars in the computer processing means, which in turn are capable of generating a list of the jars containing biological samples having led to the establishment of a diagnosis, for example at least two weeks before the date on which the list is generated.

Regarding the final steps of the present method, it should be noted that the invention has provided that advantageously, during the detection of said given event, it is possible to automatically trigger the means for indicating the position of the jars 3a, 3b, 3c to be extracted that are included by said container 4, allowing an operator to identify the jars to be destroyed at a glance. This saves him from using the list displayed on the screen of the barcode reader or the computer.

According to an additional alternative, during the detection of said given event, it is also possible, in the context of the present method, to trigger means for automatic extraction of the jars 3a, 3b, 3c from the container 4 of the equipment item 1, thus avoiding any manual intervention by an operator.

We claim:

1. A system for automatically managing a plurality of biological samples, the system comprising:

a sample jar being comprised of a bottom, a peripheral wall on top of said bottom, and a lid opposite said bottom so as to close a respective biological sample in said sample jar, wherein encoded identification data is affixed on at least one of said peripheral wall and said lid;

a storage container being comprised of a plurality of housings, wherein a first housing of said plurality of housing has a first shape complementary to said bottom of said sample jar and a first position marking on said storage container corresponding to said first housing, wherein said position marking is comprised of at least one of a group consisting of: a raised shape and a recessed shape;

a case defining a cavity, said storage container being removably accommodated within said cavity;

means for reading said encoded identification data, being within said case;

means for reading position markings, being within said case;

means for rotating said storage container, being within said cavity so as to detect said encoded identification data of said sample jar with said means for reading said encoded identification data and said first position marking of said first housing of said plurality of housings with said means for reading position markings; and a computer processing means being in communication with said means for reading said encoded identification data and said means for reading position markings and being comprised of processor with a software application, a memory, and a user interface, wherein said computer processing means in communication with said means for reading said encoded identification data and said means for reading position markings is configured to store said encoded identification data of said sample jar for said respective biological sample, said first position marking of said first housing of said plurality of housings for said respective biological sample, and history data of said respective biological sample, in said memory, and configured to determine a confirmed location of said respective biological sample with said processor according to said encoded identification data and said first position marking, and wherein said computer processing means is configured to determine a list comprised of history data comprised of a given event for said respective biological sample and any biological sample with said given event with said user interface and said processor.

2. The system, according to claim 1,
wherein said means for rotating said storage container is comprised of a shaft mounted rotating in said cavity,
wherein said storage container is comprised of a plate having a lower face and an upper face opposite said lower face, said plurality of housings being accessible to said sample jar on said upper face, and
wherein said means for rotating said storage container is further comprised of an assembly means for said shaft and said plate being in removably attached and rotational engagement.

3. The system, according to claim 2,
wherein said shaft is comprised of a free end and an end piece with a polygonal cross section on said free end,
wherein said plate is comprised of an orifice complementary to said polygonal cross section of said end piece, said orifice extending from said lower face toward said upper face, the assembly means being comprised of said end piece and said orifice.

4. The system, according claim 1, wherein a second housing of said plurality of housings has a second shape complementary to respective bottom of another sample jar and a second position marking on said storage container corresponding to said second housing, said second shape being different from said first shape, said another sample jar being different form said sample jar, and
wherein rotation of said means for rotating said storage container for said first housing is different for said second housing.

5. The system, according to claim 1, further comprising: mistake-proofing means for positioning said sample jar in said first housing,
wherein said peripheral wall and said bottom form a sample jar shape, the mistake-proofing means being comprised of said sample jar shape and said first shape of said first housing.

6. The system, according to claim 1, further comprising: an additional encoded data reader in communication with said computer processing means.

7. The system, according to claim 1, wherein said first housing has a first indicator means on said storage container corresponding to said first housing, being in communication with said computer processing means,
wherein said computer processing means is configured to activate said first indicator means when said respective biological sample is on said list.

8. The system, according to claim 1, further comprising: means for automatically extracting jars from said storage container, being in communication with said computer processing means,
wherein said computer processing means is configured to remove said sample jar with said means for automatically extracting jars when said respective biological sample is on said list.

9. The system, according to claim 1, further comprising: a furniture component, said storage container being removeably housed in said furniture component with additional storage containers.

10. A method for automatically managing a plurality of biological samples, the method comprising the steps of:
placing a biological sample in a sample jar of a system of claim 8;
reading said encoded identification data by rotating said storage container;
reading said first position marking by rotating said storage container;
communicating said encoded identification data; and said first position marking to said computer processing means to determine a confirmed location of said biological sample with said processor according to said encoded identification data and said first position marking;
detecting an occurrence of a given event in said history data;
determining said list comprised of history data comprised of said given event for said respective biological sample and any biological sample with said given event with said user interface and said processor; and
removing said sample jar from said storage container with said means for automatically extracting jars when said respective biological sample is on said list so as to destroy said biological sample.

11. The method according to claim 10, wherein said first housing has a first indicator means on said storage container corresponding to said first housing, being in communication with said computer processing means, the method further comprising the steps of:
activating said first indicator means when said respective biological sample is on said list wherein the step of activating is immediately after the step of determining said list.

12. The method according to claim 10, wherein the step of removing said sample jar is immediately after the step of determining said list.

* * * * *